United States Patent [19]

Davis et al.

[11] 4,303,885
[45] Dec. 1, 1981

[54] DIGITALLY CONTROLLED MULTIFREQUENCY EDDY CURRENT TEST APPARATUS AND METHOD

[75] Inventors: Thomas J. Davis; Charles B. Perry, both of Richland, Wash.

[73] Assignee: Electric Power Research Institute, Inc., Palo Alto, Calif.

[21] Appl. No.: 49,192

[22] Filed: Jun. 18, 1979

[51] Int. Cl.³ .................... G01R 33/12; G01N 27/82
[52] U.S. Cl. ................................... 324/237; 324/225; 324/232; 324/233; 324/240
[58] Field of Search ........ 324/232, 233, 234, 237–243, 324/225–228

[56] References Cited

U.S. PATENT DOCUMENTS

| | | | |
|---|---|---|---|
| 3,337,796 | 8/1967 | Hentschel et al. | 324/233 |
| 3,405,354 | 10/1968 | Callan et al. | 324/233 |
| 3,478,263 | 11/1969 | Hentschel | 324/233 |
| 3,701,941 | 10/1972 | Bantz et al. | 324/238 |
| 4,059,795 | 11/1977 | Mordwinkin | 324/233 |
| 4,061,968 | 12/1977 | Pigeon | 324/234 |
| 4,207,520 | 6/1980 | Flora et al. | 324/233 X |

Primary Examiner—Gerard R. Strecker
Attorney, Agent, or Firm—Flehr, Hohbach, Test

[57] ABSTRACT

Digitally controlled eddy current test apparatus for detecting flaws, their extent and location. The apparatus provides absolute and differential measurements. The apparatus employs multi-frequencies with the signals from the test coils mixed in a predetermined manner to reduce unwanted signals such as may be introduced by wobble (lift-off) and support plates.

26 Claims, 14 Drawing Figures

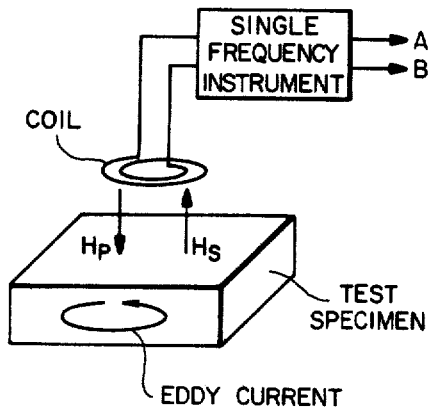
FIG__1
(PRIOR ART)
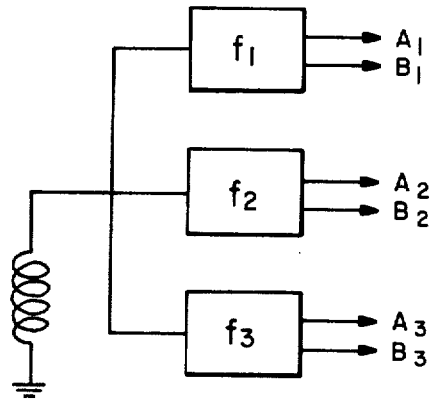
FIG__2
(PRIOR ART)
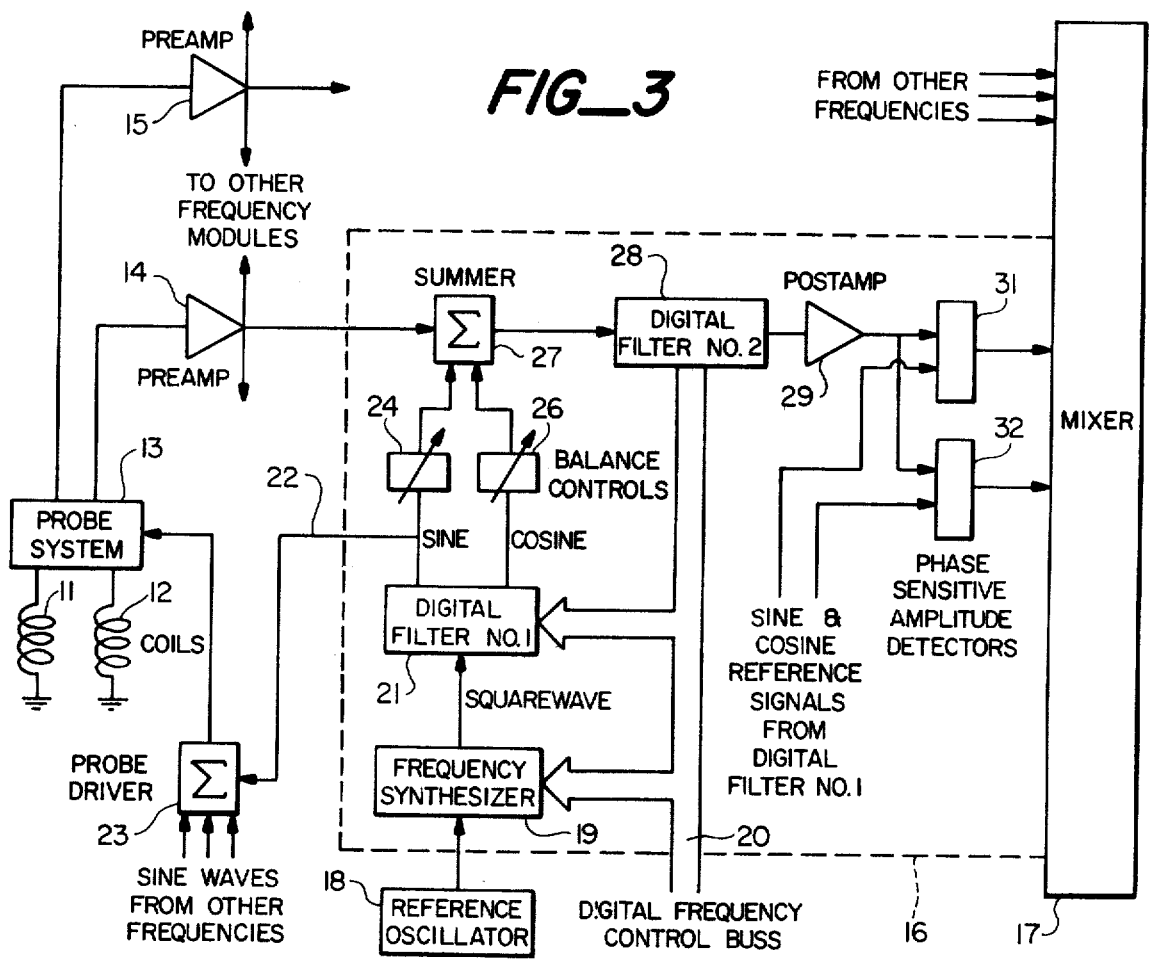
FIG__3

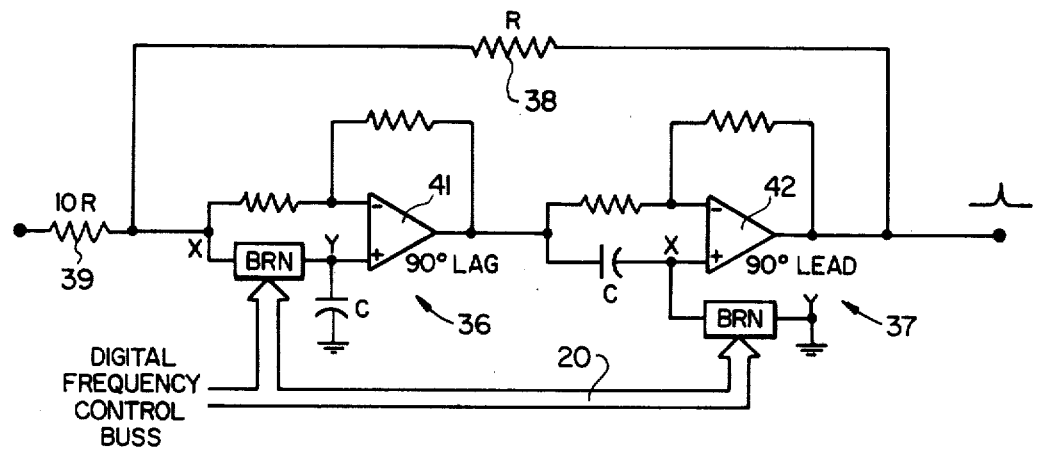
FIG_4
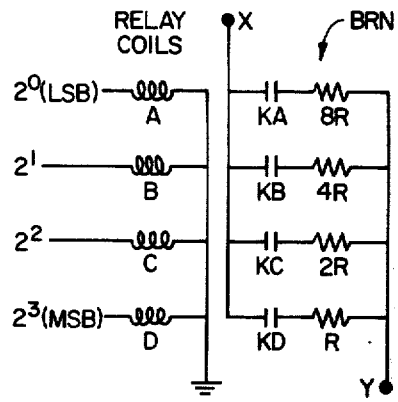
FIG_5
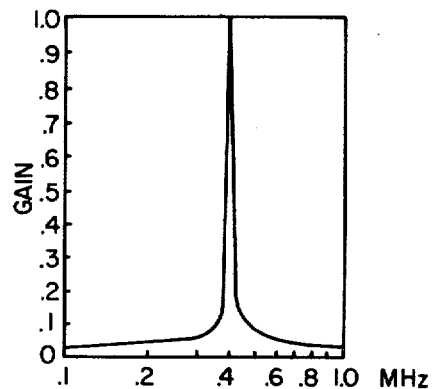
FIG_6
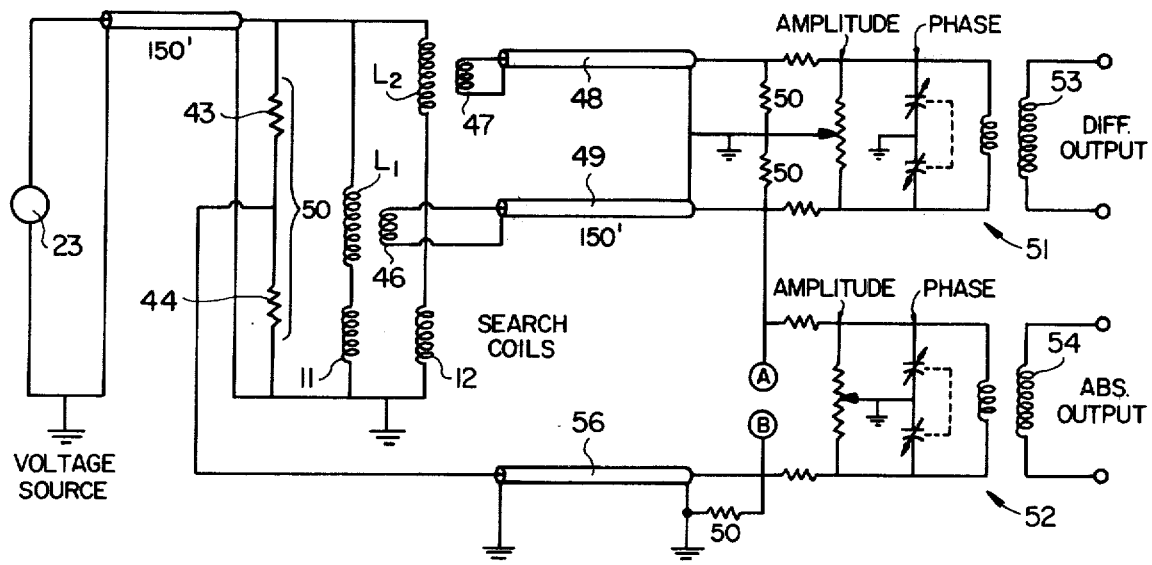
FIG_7

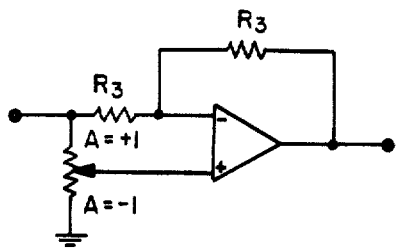
FIG_8
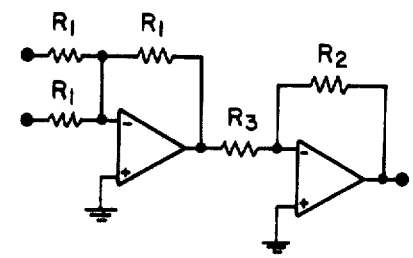
FIG_9
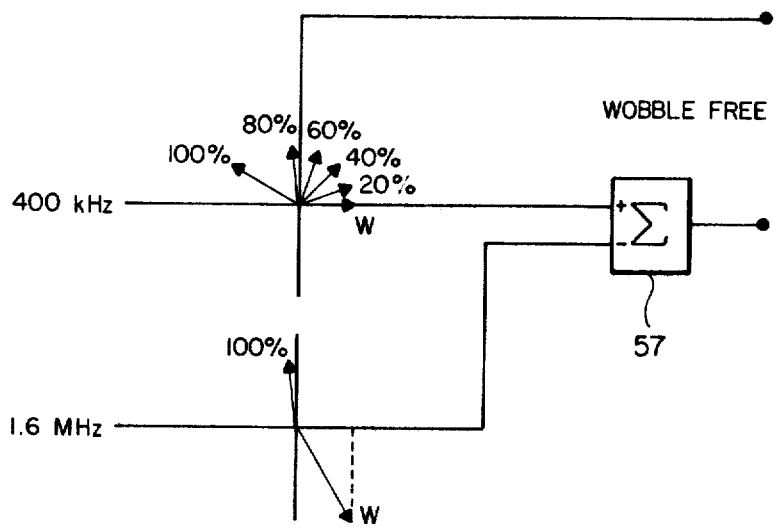
FIG_10
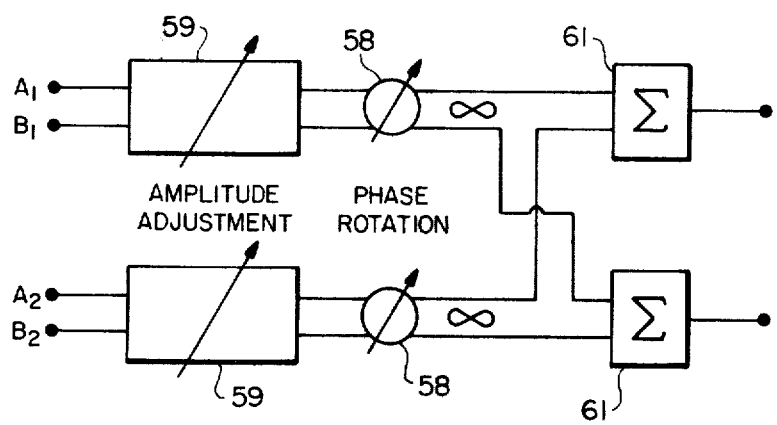
FIG_11

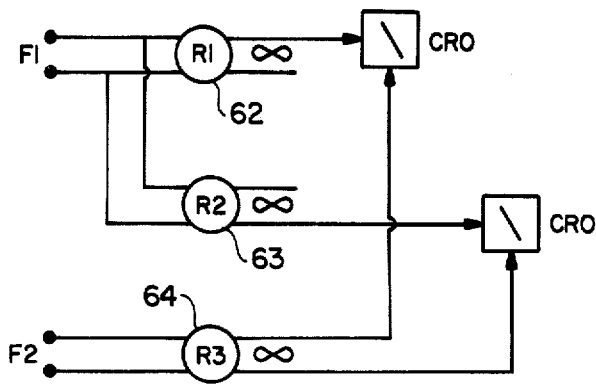
FIG_12
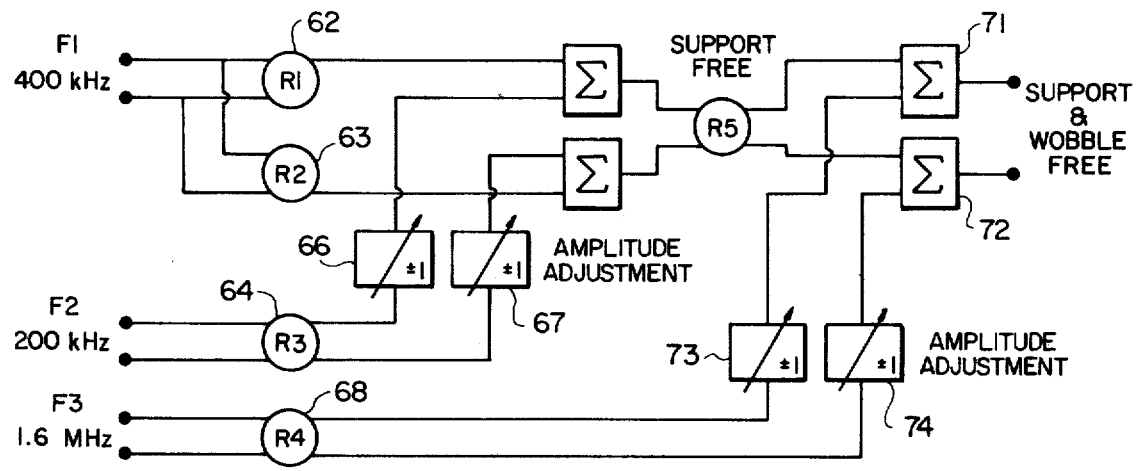
FIG_13
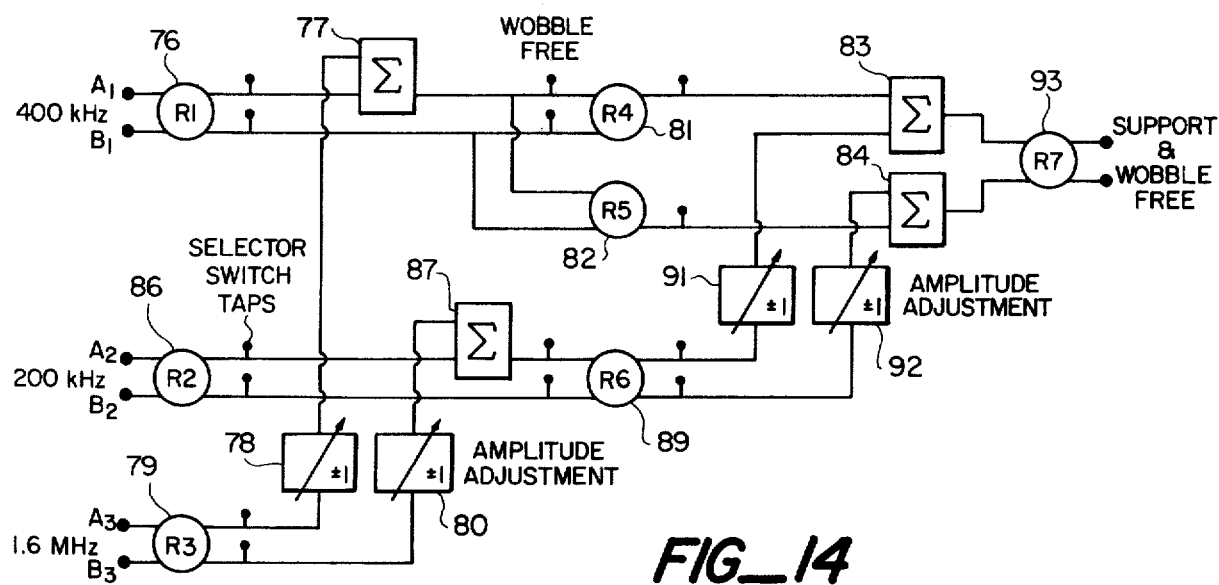
FIG_14

DIGITALLY CONTROLLED MULTIFREQUENCY EDDY CURRENT TEST APPARATUS AND METHOD

This invention relates generally to a non-destructive testing employing eddy current and more particularly to apparatus for obtaining absolute and differential measurements of desired parameters such as flaw location and depth and wall thickness while eliminating unwanted parameters such as support signals and probe wobble signals.

The principles of electromagnetic non-destructive testing are well known. More specifically, in such tests eddy currents are caused to flow within an object to be tested by induction from an adjacent coil which is excited by an alternating current. The eddy currents generate magnetic fields which couple to the coil and induce voltages within the coil. The eddy current magnetic fields induce voltage in the coil which is at the same frequency as that of the excitation current but which may be a different phase angle. The phase angle and amplitude of the induced voltage depend upon the characteristics of the object under test. The induced voltage may be measured by suitable electronic equipment and is detected either as variations in voltage or equivalent impedance of the coil. The induced voltage will vary with the test coil to object magnetic coupling and by the characteristics of the object being scanned. Thus, changes in dimensions, variations of electrical conductivity, cracks, spacing of the coil and the like will all modify the intensity of the eddy currents as the coil is moved past the object under test. The change of impedance or voltage due to the reflected eddy current magnetic field gives indication of dimension, variations in spacing, conductivity, cracks, etc. When employing single frequency testing it becomes virtually impossible to discriminate between the various parameters which cause the change in impedance or current. To overcome this problem the coil is excited with a number of frequencies and the signals combined to cancel out unwanted test parameters while retaining those of interest.

Multi-frequency eddy current testing is generally implemented by simultaneously operating two or more single frequency instruments with a common probe or coil system. Two parameters, A and B, are output from each frequency, namely the in-phase and quadrature components of the search coil impedance or voltage. These outputs are the Fourier amplitude coefficients of the coil signal and are related to eddy currents flowing in the test specimens as follows:

$$A \cos \omega t + B \sin \omega t = kH_s \tag{1}$$

where k is a proportionality factor, $H_s$ is the field generated by eddy currents, $\omega$ the frequency and t the time.

To aid in an understanding of the foregoing, FIG. 1 shows a schematic diagram of a single frequency single coil eddy current test system.

The system shown operates substantially as follows (1) The search coil is excited with an alternating current at the test frequency and positioned over the specimen. (2) The primary field $H_p$ of the coil links and produces a potential difference in the conducting specimen. The potential differences in the specimen cause circulating or eddy currents to flow in the specimen. (3) The eddy currents produce a secondary electromagnetic field $H_s$. This field links with the search coil and induces secondary voltages within the coil. (4) The secondary voltages are detected as a change in equivalent impedance of the coil. Generally, the coil is connected to one leg of an impedance bridge. The induced secondary voltages in the coil result in a change in the volt-amp characteristics of the coil with respect to the instrument, and hence in a change of the equivalent impedance of the coil. This change is then detected by suitable associated circuitry. Alternately, the secondary voltages may be detected directly by a second coil coupled to the search coil and employed to provide an indication of the phase and amplitude of the eddy currents. (5) The quadrature Fourier amplitude coefficients A and B of the secondary voltages are then detected and provided as outputs by the instrument. In the prior art these are used to interpret a variety of material properties including conductivity, permeability, thickness, flaws, voids or inclusions and probe-to-specimen spacing lift-off, each of these being absolute measurements.

In FIG. 2 there is illustrated schematically a prior art multi-frequency test system. The amplitude coefficients A and B for each frequency are simultaneously provided in real time. They are then combined or mixed in real time by analog arithmetic circuitry to obtain the desired cancellation of unwanted parameters. The combination process may be likened to the simultaneous solution of multiple equations in which variables are eliminated by multiplying certain equations by an appropriate constant and adding the result to other equations. Depending upon the test requirements, the optimal signal combinations must be selected with caution. In general, there can be a wide variety of ways to combine the output for the various frequencies to cancel given parameters. Not all of such combinations will provide meaningful or high sensitivity information. Computer optimization techniques have been successfully used in many cases to determine the optimum combination. Single coils are used to obtain absolute measurements of object parameters such as conductivity and dimensional measurements. A pair of coils may be used in a differential arrangement. The coils are connected in a bridge circuit so that a null signal is obtained if both coils are presented with the same test object conditions. Thus this arrangement can be used to discriminate against slow varying conditions along a tubing or bar of material.

In accordance with the present invention, there is provided an improved digitally controlled multi-frequency eddy current test system.

The dual coil system in accordance with the present invention can be operated simultaneously in both differential and absolute test modes. The absolute test can be used to give a continuous profile of wall thickness and medium to large flaws in tubing while the differential test can be used to detect small flaws such as stress corrosion cracks.

The probe circuit provides matched transmission lines for exciting the probe and for obtaining of signals to avoid resonant circuit problems where long cable lengths are involved.

The digital system includes bandpass filters with digitally controlled center frequencies and sine and cosine outputs.

A mixer is provided for the multi-frequency signals which obtains a maximum reduction of unwanted parameters with improved sensitivity. More particularly probe wobble (lift off) if compensated without altering the basic phase shift versus flaw depth response obtained from a single frequency response. The response from tubing support plates is also significantly reduced.

FIG. 1 schematically shows the implementation of a single frequency eddy current test.

FIG. 2 shows a multi-frequency eddy current test system.

FIG. 3 is a block diagram of an eddy current test system in accordance with the invention.

FIG. 4 shows a digitally controlled bandpass filter used in the system of FIG. 3.

FIG. 5 shows the binary resistor network (BNR) of FIG. 4.

FIG. 6 shows the frequency response of the filter of FIG. 4.

FIG. 7 shows the differential-absolute probe system of the present invention.

FIG. 8 shows a variable gain amplifier for use in the mixing networks of the present invention.

FIG. 9 shows a summing amplifier for use in the mixing networks of the present invention.

FIG. 10 is a vector diagram illustrating wobble cancellation in accordance with the invention.

FIG. 11 shows a two frequency mixing circuit for elimination of parameters having complex output indications.

FIG. 12 shows a support cancellation technique.

FIG. 13 shows a three frequency mixing system in accordance with the invention.

FIG. 14 shows a three frequency mixing system in accordance with another embodiment of the invention.

FIGS. 1 and 2 have been described above. FIG. 3 is a block diagram of a non-destructive eddy current testing system in accordance with the present invention. The system includes means for exciting differential coils, sensing signals induced on the coils by eddy currents, obtaining the Fourier amplitude coefficients A and B of the induced signals and applying them to a mixer which eliminates unwanted parameters.

The system includes a pair of coils 11 and 12 which may be suitably mounted as, for example, which may be inserted into and moved along steam generator tubing. The coils are connected to a probe excitation and signal recovery circuit 13 to be presently described, FIG. 5. The outputs of the circuit 13 are applied to preamplifiers 14 and 15 and then applied to processing modules, one for each frequency. One such module is shown in the dotted box 16. The output from each module is applied to a mixer 17 which, as previously described, serves to process and combine the signals to eliminate unwanted parameters.

Each module receives an input frequency from a reference oscillator 18. The oscillator may be a crystal-controlled oscillator providing a fixed output frequency to a frequency synthesizer 19. The frequency synthesizer is responsive to digital control signals applied along the control buss 20 and generates a squarewave at a frequency determined by the digital command. The digital buss 19 is also connected to a digital filter 21 to be described in more detail with reference to FIGS. 4 and 5. The digital filter filters the squarewave and provides output sinusoidal signals having sine and cosine relationship. The sine output is applied along the line 22 to a summing amplifier which serves as the probe driver to excite the coils. The sine and cosine signals are also applied to balance controls 24 and 26 connected to a summing amplifier 27. Sine outputs from other modules at other frequencies are also applied to the amplifier 23 and excite the coils at other selected frequencies. The signal output from the probe circuit preamplified by amplifier 14 contains all of the input frequencies to the probe. If the description to follow, three signal frequencies have been selected, namely, 400 kH$_z$, 200 kH$_z$ and 1.6 MH$_z$. However, more or less signal frequencies may be applied to the summing amplifier 23. The output which includes all the frequencies is applied to a summing amplifier 27. The quiescent signals of the in-phase and quadrature voltages in the test signal not eliminated by the probe circuit are nulled out by adding equal but opposite values of sine and cosine signals derived from the balance controls 24 and 26. The balance controls establish the proper value of the signals input to the summing amplifier 27 to perform the nulling operation for the module frequency signals.

Other test frequencies are stripped from the nulled signal by the digitally controlled filter 28 which is controlled by the digital control buss 19. Output of the digital filter is amplified by amplifier 29 and applied to a pair of phase sensitive amplitude detectors 31 and 32 which receive sine and cosine reference signals from filter 21. The phase sensitive amplitude detectors extract the Fourier amplitude coefficients A and B from input signal E sine ($\omega t + \theta$):

$$A = E \text{ cosine } \theta,$$

and $$B = E \text{ sine } \theta.$$

The output signals from the detectors 31 and 32 are applied to the mixer 33 together with signals from other modules 16. The other output signal frequencies from the probe circuit are processed in an identical manner to provide A and B Fourier amplitude coefficients for each frequency to a mixer.

The digitally controlled filters 21 and 28 provide several important functions in the eddy current system. Each filter can provide a high Q bandpass response such as the response shown in FIG. 6. A suitable filter is shown in FIG. 4. The filter provides both sine and cosine outputs which are useful as null balancing signals for the summing amplifier 27 and as reference signals for the phase sensitive amplitude detectors 31 and 32. The center frequency of the filter can be controlled by digital commands so that the test frequency can be changed without manual retuning. This same digital control signal also controls the test frequency through use of the frequency synthesizer 19. Consequently, both the filters and the test frequency track a single frequency control.

The basic filtering concept employs phase shifting and positive feedback and has been described in the literature; for example, one scheme has been described in the article by U. Thoren entitled "Banish Inductors from Resonant Circuits", Electronic Design No. 17, Aug. 16, 1973, pp. 72-74. A circuit diagram of the filter is shown in FIG. 4. The filter uses two conventional constant amplitude phase shift circuits 36 and 37 to obtain 90° of lag and lead respectively. These phase shifters are tied into a feedback system including the resistor 38 to obtain a Q multiplier effect. The transfer function of the filter is:

$$V_{out} = \frac{AV_{in}}{1 + \frac{R_{in}}{R_f}(1-A)}$$

Where A is the open loop vector gain. This assumes that the input resistor 39 shown as 10R in the figure is not loaded by the input of the first phase shifter. In practice, a buffer may be placed ahead of the first phase shifter 36. The phase shifters 36 and 37 are unity gain devices, and at the center frequency (where the reactance of capacitor C is equal to the resistance of the binary resistance network) the open loop gain will have a value of 1+jo; the output will equal the input. As the input frequency deviates from the center frequency, the open loop gain acquires phase shift and the transfer function diminishes rapidly.

Frequency control is accomplished by switching a set of binary weighted resistors in a binary resistor network BRN. The resistors are shown in FIG. 5 connected to relay contacts KA, KB, KC and KD. The resistor network is connected between the points X and Y, FIG. 4. The relays are controlled by digital signals which are applied via the digital buss 19 to the relay coils A, B, C and D to close the associated contacts.

The center frequency of the filter is $$f_o = \frac{D}{16\pi RC}$$

where D is the value of the digital word (1 through 10) applied to the network and R and C are the components shown in FIG. 4.

In practice, the resistor network is used to cover a decade of frequency and decade changes can be implemented by switching in other values of capacitance via solid state relays (not shown). The cosine wave for null balancing and detector references can be extracted from the output of the first phase shifter 36. The filters 27 and 28 of module 16 are of the above type as are the filters for other modules operating at different frequencies.

As previously stated, the probe circuit and its operation will now be described. A detailed circuit diagram of the probe circuit 13, FIG. 3, is shown in FIG. 7. The circuit provides both differential and absolute output signals. Furthermore, the circuit permits the use of long cables between the coils 11 and 12 and the balance components located at the test location. In the prior art parallel resonance occurred at a frequency where the coil reactance equalled the cable's capacitive reactance. Additionally, for high test frequencies prior art cables acted as transmission lines have unmatched terminations, and produced quarter wave and half wave resonances. Furthermore, in the prior art it was not possible to extract a signal from a single coil for absolute testing in a differential coil system.

The new probe system shown in FIG. 7 overcomes the above disadvantages. An impedance bridge is formed by placing inductors $L_1$ and $L_2$ which have inductances equal to those of the search coils, in series with the search coils 11 and 12. The bridge is driven by the probe driver 23 through a cable which is terminated at the coils in 50 ohms represented by resistors 43 and 44. The cable extends from the test location to the coils which may be 150 or more feet away.

The desired outputs of the bridge are the voltage across each of the search coils. As shown in the figure, these are obtained by winding small secondary inductors 46 and 47 on inductors $L_1$ and $L_2$. If the secondaries have substantially fewer turns than do $L_1$ and $L_2$, they will have a minimal effect on the bridge when loaded with a 50 ohm transmission line or cable. For example, a 4:1 stepdown turns ratio will result in the equivalent of an 800 ohm load being placed in shunt with $L_1$ and another with $L_2$. This will cause minimal loading except for very high frequencies where the inductive reactances of $L_1$ and $L_2$ begin to approach 800 ohms.

The outputs of the secondaries will remain proportional to the search coil voltages over a wide range of frequencies. An alternate method for tapping the bridge lies in winding a secondary on each search coil with the secondaries again having substantially fewer turns than the search coils. This method will perform over a very large frequency range because it is not dependent upon the reactance of the search coils being larger than the 50 ohm source impedance.

The secondary voltages may be brought back to the instrument balancing network 51 on cables 48 and 49 terminated with their characteristic impedance. One of the signals may be fed to a second balancing network 52 to obtain an absolute (single coil) test. Both tests may be performed at the same time if desired. Step-up transformers 53 and 54 on the output of the balance networks recover the sensitivity lost by step-down action of the coils 46 and 47.

The balance network operates by equalizing the amplitude and phase of the two secondary voltages so that no quiescent signal appears across the output transformer. A similar network may be used to implement the simultaneous absolute test with the exception that one of the inputs is derived from the driving voltage instead of the probe inductors. In some applications, it is desirable to derive this voltage by tapping off part of the drive signal appearing on the 50 ohm terminating resistor at the coils. This 50 ohm resistor may be made up of two resistors which form a voltage divider and provide a low level output for transmission back to the balance network via the cable 56. This approach has the advantage that both the coil signal and the reference signal have undergone the same propagation delay in coaxial cables, and thus, a null balance is much easier to obtain due to phase matching of the signals.

As previously described, the output signals of the detectors 31 and 32 are applied to a mixer. These signals may include information regarding a number of parameters some of which are desired and some of which interfere with the measurement of the desired parameter.

Reduction of unwanted parameters in multifrequency eddy current testing is performed by making linear combinations of data from individual frequencies. The combination process is generally referred to as mixing. Three circuit devices are commonly used in the mixing process. These are: (1) phase rotators, (2) variable gain amplifiers, and (3) summing amplifiers.

A phase rotator is a device having two input ports X and Y and two output ports $X^1$ and $Y^1$. Its transfer function is:

$$X^1 = X \cos\theta - Y \sin\theta$$

$$Y^1 = Y \cos\theta + X \sin\theta$$

where $\theta$ is the desired rotation angle.

The two outputs from each test frequency are usually treated as a two dimensional cartesian coordinate system and are analyzed by plotting them on an X-Y oscilloscope. The phase rotator serves to rotate the displayed pattern about the axes by the angle $\theta$.

Suitable variable gain amplifiers and summing amplifiers are shown in FIGS. 8 and 9 respectively.

The basic procedure for elimination of an unwanted response is to rotate and size the individual indications from each frequency until they are opposite in polarity and equal in size. The horizontal and vertical (X and Y) from each frequency are then combined in summing amplifiers to produce two new output channels which are relatively free of the unwanted response. Selection of frequencies plays an important part in insuring that the final outputs still contain useful data on the test parameters. In the case of tubing inspection, the skin effect provides differing phase shift versus flaw depth responses so that some linearly independent information is available for the mixing process.

The new mixing methods described herein were developed specifically for inspection of nonferrous tubing using an internal probe. The advantages they provide over conventional mixing techniques are: (1) probe wobble (the liftoff effect) is compensated for without altering the basic phase shift versus flaw depth response obtained from a single frequency test; and (2) the response from a tubing support plate can be reduced by 90 to 95%. These results are quite important in the inspection of steam generator tubing in nuclear power plants because wobble and support indications can mask many flaw responses and render the flaws either undetectable or unsizable.

The wobble cancellation technique is illustrated in FIG. 10.

Vector responses (X/Y plots) are shown for the conventional 400 kHz single frequency test with OD calibration flaw depths indicated in percent wall thickness. The pattern has been rotated to place wobble (W) in the horizontal channel, and the figure-eight flaw patterns are represented by a single vector of proper amplitude and phase. Under present in-service inspection with single frequency testing, the data interpreter assesses flaw depth by measuring the phase angle of flaw indications displayed in an X Y format with the same orientation shown in the figure.

As the test frequency is changed, the relationship between the 100% flaw and wobble remains essentially unchanged while the phase spread for other flaw depths increases or decreases with frequency due to the skin effect. Unfortunately, this means that different frequencies will not produce independent information for eliminating wobble without altering the 100% flaw response drastically during mixing. In practice, when another frequency in the 100 to 600 kHz range was used to cancel wobble from the 400 kHz response, the combination produced an output in which the 100% flaw indication lay between the 80 and 60% responses. Additionally, the phase shift versus flaw depth response was reduced by 60%, resulting in decreased accuracy.

This problem was overcome in the present invention by selecting a second frequency (1.6 MHz) which is high enough so that the skin effect eliminates all but the 100% flaw. The pattern is rotated until the 100% flaw is primarily contained on one of the axes and is sized until the wobble component projected on the other axis is equal to that of the 400 kHz response. This is illustrated in the lower part of the figure. This signal is then subtracted from the 400 kHz horizontal channel in the summing amplifier 57 to obtain a 400 kHz output with wobble eliminated and which features minimal pollution of the 100% response.

When the two outputs of a conventional single frequency steam generator tubing test are viewed on an X-Y oscilloscope, the indication from a tube support is large enough to mask signals from flaws which may be located under or adjacent to the support plate. Support plates are typically made of mild steel which is 1 82 inch thick and which has a pattern of holes through which the tubes pass. In the case of an absolute (single coil) test, the X-Y support indication is a deviation from the zero point which possesses substantial curvature. For a differential test, the support response is a figure-eight Lissajous pattern as viewed on an oscilloscope.

FIG. 11 shows how conventional two-frequency mixing is performed to reduce the amplitude of the support signal for a differential test. The indications from the two frequencies are rotated by phase rotators 58 and sized by varying the gain of amplifiers 59 until they are approximately equal and out of phase. The horizontal and vertical components are then summed in summing amplifiers 61 to generate the mixed outputs. In practice, this mixing technique can produce a 70 to 80% reduction of the support signal.

The following disclosure describes a mixing technique which can achieve a 90% reduction of support amplitude in one output channel and a 95% reduction in the other. This results in higher detectability and more accurate sizing of flaws located in the support region.

The basis of the new technique is shown in FIG. 12. The technique accommodates the fact that the support signals from different frequencies are not exact replicas of each other due to skin effect phenomena in the tube wall. The technique permits the best possible support reduction to be achieved by direct observation of the signals to be summed. The observation is performed in such a manner that the phase rotators 62 and 63 can be rapidly and easily adjusted to their optimum settings. Furthermore, an additional phase rotator 64 is used so that independent adjustments may be made for the high degree of support elimination that the method achieves.

The two rotators 62 and 63 shown in the F1 channel are adjusted until the support signals are horizontally oriented when their outputs are viewed on an X-Y oscilloscope. The rotator 64 in the F2 channel is adjusted to place the support signal horizontal and out of phase with those of the F1 channel. The horizontal outputs from each frequency are then viewed on an X-Y oscilloscope and rotator 62 is adjusted until the pattern assumes a straight line when the probe is drawn past a support. When this condition is met, the two horizontal support signals are linearly related to each other as a function of probe position and will be effectively cancelled when summed together with the proper weighting coefficients. A similar viewing process is performed on the vertical support channels while rotator 63 is adjusted for optimum linearity of the displayed response. The optimized horizontal and vertical channels are then respectively summed together after multiplication by the proper weighting coefficients as shown in FIG. 13. In the arrangement shown, the weighting coefficients 66 and 67 are applied to the F2 frequency channels so that the support indications on these channels are equal but of opposite polarity to those on the F1 frequency channels.

The summed output signals are support free channels which still contain information on tube flaws and probe wobble. FIG. 13 shows how the wobble cancellation technique described earlier is applied to these channels. Rotator 68 and the two output summing amplifiers 71 and 72 and weighing amplifiers 73 and 74 shown are used in the wobble elimination process.

In an alternate mixing method, the wobble can be removed from F1 and F2 data prior to support cancellation. This permits easier setup of the support cancelling arrangement but requires a larger parts count.

FIG. 14 shows the alternate system with the preferred frequencies of operation 200 kHz, 400 kHz and 1.6 MHz. The 400 kHz signal $A_1$, $B_1$ is rotated by rotator 76 to provide a wobble prone and wobble free output. The wobble prone output is applied to summing amplifier 77 which receives an input from the variable gain amplifier 78 connected to rotator 79 which receives the 1.6 MHz signal $A_3$, $B_3$. A wobble free output is generated which is applied to the rotators 81 and 82 along with the wobble free output from rotator 76. The wobble free outputs of the rotators 81 and 82 are applied as one input to summing amplifiers 83 and 84.

The 200 kHz signals $A_2$, $B_2$ are rotated by rotator 86 to form wobble prone and wobble free signals. The wobble prone signal is combined in summing amplifier 87 with a signal derived by variable gain amplifier 88 from the output of rotator 79 to form a wobble free output. The wobble free outputs from rotator 86 and summing amplifier 87 are applied to rotator 89. The wobble free outputs of rotator 89 are applied to the summing amplifiers 83 and 84 through variable gain amplifiers 91 and 92. The outputs from variable gain amplifiers 91 and 92 are adjusted so that when they are summed with the other inputs to the summing amplifiers 83 and 84 the output of the summing amplifiers is essentially support free. The support free, wobble free signals are then applied to the rotator 93 whose output is applied to a readout oscilloscope or other device to give a reading of flaw depth.

The same mixing circuits can be used to provide signals for desired parameters while eliminating undesired parameters for both the absolute or differential signals.

What is claimed is:

1. A digitally controlled eddy current test apparatus including at least one coil adapted to be coupled to an object to be tested to induce eddy currents in said object which in turn induce voltages in said coil or in a sensing coil comprising
    means for receiving and providing a digital frequency control signal,
    a frequency synthesizer connected to receive said digital frequency control signal and provide an output signal at frequency $f_1$ determined by said digital frequency control signal,
    a first digital filter connected to receive said digital frequency control signal and said output signal and having its center frequency controlled by said digital control signal whereby to be tuned to the frequency of said output signal and provide sine and cosine output signals,
    means for receiving one of said sine of cosine outputs and applying the same to said coil to induce eddy currents in said object,
    means for receiving the voltage induced by the eddy currents in said object in said coil or sensing coil to null out in-phase and quadrature quiescent components from said induced voltage to produce a nulled output signal $E_1 \sin(\omega t + \theta)$
    a second digital filter having its frequency controlled by said digital frequency control signal serving to filter said nulled input signal and pass only signals of said frequency $f_1$, and
    phase sensitive detectors connected to receive said filtered nulled signal and sine and cosine signals from said first digital filter and provide Fourier amplitude coefficients $A_1$ and $B_1$ of the coil voltage at the frequency $f_1$ where $A_1 = E_1 \cosine \theta$ and $B_1 = E_1 \sine \theta$.

2. An eddy current test apparatus as in claim 1 including at least two test coils adapted to be coupled to said object and connected in series each with a fixed coil and the series combination being excited by said sine or cosine applied signal, means including secondary windings one associated with each series combination for providing an output signal indicative of the voltage induced on each of said test coils, a first nulling bridge connected to receive the signals from said secondary windings and provide an output and a summing amplifier connected to receive the output from said bridge and said sine and cosine signals from said first digitally controlled bandpass filter and serving to null out quiescent voltages and provide the output to said second digitally controlled filter.

3. An apparatus as in claim 2 including second bridge means connected to receive the signals from one of said secondary windings and a signal indicative of the exciting voltage to the coils and providing an output which provides an absolute output signal.

4. An apparatus as in claim 3 including means for receiving said absolute signal and processing same to provide Fourier amplitude coefficients A and B.

5. An eddy current test apparatus as in claim 1 including a plurality of processing modules operating at test frequencies $f_1$ and $f_2$ to provide exciting signals at frequencies $f_1$ and $f_2$ to said coil and to generate output Fourier coefficients $A_1, B_1$ and $A_2, B_2$ and means for receiving said amplitude coefficients and combining them in a predetermined manner to eliminate and cancel unwanted parameters.

6. An eddy current test apparatus as in claim 1 including a plurality of processing modules operating at test frequencies $f_1, f_2$ and $f_3$ wherein $f_3$ is a substantially higher frequency than $f_1$ and $f_2$ so that the skin effect eliminates all but near surface indications for the frequency $f_3$, said modules providing output coefficients $A_1$, $B_1$, $A_2$, $B_2$, $A_3$, $B_3$,
    means for receiving said output coefficients $A_1$, $B_1$, $A_2$, $B_2$, $A_3$, $B_3$ and combining said coefficients in a predetermined manner to provide an output which is indicative of flaws and insensitive to support and probe wobble or lift off variations.

7. An eddy current test apparatus as in claim 5 including at least two test coils adapted to be coupled to said object connected in series each with a fixed coil and the series combination being excited by said sine or cosine applied signal, means including secondary windings one coupled with each series combination for providing an output signal indicative of the voltage induced on each of said test coils, a first nulling bridge connected to receive the signals from said secondary windings and provide an output from said bridge and said sine and cosine signals from said first digitally controlled filter and serving to null out quiescent voltages and provide the output to said second digitally controlled filter.

8. An apparatus as in claim 7 including second bridge means connected to receive the signals from one of said secondary windings and a signal indicative of the exciting voltage to the coils and providing an output which provides an absolute output signal.

9. An eddy current test apparatus as in claim 2 in which said nulling bridge is connected to said secondary windings by coaxial cables terminated in their characteristic impedance.

10. An eddy current test apparatus as in claim 3 in which said signal indicative of exciting voltage is applied to said second bridge by a coaxial cable terminated in its characteristic impedance.

11. An eddy current test apparatus as in claim 8 in which said nulling bridges are connected to the secondary windings and to the exciting signal by coaxial cables terminated in their characteristic impedance.

12. An eddy current test apparatus as in claim 5 in which said means for combining the Fourier amplitude coefficients include amplifying means and phase rotating means.

13. An eddy current test apparatus as in claim 6 in which said means for combining said Fourier amplitude coefficient signals include a first pair of amplifying means and phase rotating means connected to receive and process two of said signals and provide fourth Fourier amplitude coefficient signals and means for receiving the other amplitude coefficient signals and the fourth amplitude coefficient signals and provide fifth Fourier amplitude coefficients.

14. An eddy current test apparatus as in claim 2 in which the secondary windings are coupled to the fixed coil.

15. An eddy current test apparatus as in claim 2 in which the secondary windings are coupled to the object under test.

16. An eddy current test apparatus as in claim 1 wherein said igitally controlled bandpass filter comprises serially connected first and second constant amplitude phase shift circuits providing ninety degree phase lag and lead respectively and means providing feedback between said circuits, each of said circuits including a capacitor and a binary weighted resistor network for controlling the frequency of the circuit responsive to the digital frequency control signal.

17. An eddy current test apparatus as in claim 1 including a plurality of processing modules operating at test frequencies $f_1$ and $f_3$ where $f_3$ is substantially higher than $f_1$ to provide exciting signals at frequencies $f_1$ and $f_3$ to said coil and to generate output Fourier coefficients $A_1$, $B_1$ and $A_3$, $B_3$ and means for receiving and combining said amplitude coefficients in a predetermined manner to reduce the effect of probe wobble.

18. An eddy current test apparatus including at least one coil adapted to be coupled to an object to be tested to induce eddy currents in said object which eddy currents induce voltages in said coil or in a sensing coil comprising at least one processing module adapted to excite said coil at frequency $f_1$ and to process the voltages induced by the eddy currents in said object, means for providing a digital frequency control signal to said module to select the frequency $f_1$, said module including a frequency synthesizer adapted to receive said digital frequency control signal and provide an output signal at frequency $f_1$, a digital filter connected to receive said digital frequency control signal to be tuned to said frequency $f_1$ and serving to receive said input signal at frequency $f_1$ and provide sine and cosine output signals at said frequency, means for receiving one of said sine or cosine output signals and applying it to said coil to induce eddy currents in said object, means in said module for receiving the voltages induced by said eddy currents in said object and said sine and cosine signals and nulling out in-phase and quadrature quiescent voltages, a second digital filter responsive to said digital frequency control signal for filtering said nulled signals and providing an output signal $E_1$ sine $(\omega t + \theta)$ and phase sensitive detectors connected to receive said output signal and sine and cosine signals from said first filter and provide Fourier amplitude signals $A_1$, $B_1$ of the coil induced voltage at frequency $f_1$ where $A_1 = E_1$ cosine $\theta$ and $B_1 = E_1$ sine $\theta$.

19. An eddy current test apparatus as in claim 18 including at least two test coils adapted to be coupled to said object connected in series each with a fixed coil and the series combination being excited by said sine or cosine applied signal, means including secondary windings one associated with each series combination for providing an output signal indicative of the voltage induced on each of said test coils, a first nulling bridge connected to receive the signals from said pick-up coils and provide an output and a summing amplifier connected to receive the output from said bridge and said sine and cosine signals from said first digitally controlled filter and serving to null out quiescent voltages and provide the output to said second digitally controlled filter.

20. An apparatus as in claim 19 including second bridge means connected to receive the signals from one of said pick-up coils and a signal indicative of the exciting voltage to the coils and providing an output which provides an absolute output signal.

21. An eddy current test appparatus as in claim 18 including a plurality of processing modules operating at test frequencies $f_1$, $f_2$ and $f_3$ wherein $f_3$ is a substantially higher frequency than $f_1$ and $f_2$ so that the skin effect eliminates all but near surface indications for the frequency $f_3$, said modules providing output coefficients $A_1$, $B_1$, $A_2$, $B_2$, $A_3$, $B_3$, means for receiving said output coefficients $A_1$, $B_1$, $A_2$, $B_2$, $A_3$, $B_3$ and combining said coefficients in a predetermined manner to provide an output which is indicative of flaws and insensitive to support and probe wobble or lift off variations.

22. An eddy current test apparatus as in claim 18 including a plurality of processing modules operating at test frequencies $f_1$ and $f_2$ to provide exciting signals at frequencies $f_1$ and $f_2$ to said coil and to generate output Fourier coefficients $A_1$, $B_1$ and $A_2$, $B_2$ and means for receiving said amplitude coefficients and combining them in a predetermined manner to eliminate and cancel unwanted parameters.

23. An eddy current test apparatus as in claim 6 including means for rotating an output coefficient $A_3$, $B_3$ for frequency $f_3$ through an angle in the X-Y coordinate system so as to align the indications from near surface flaws as close as possible with one axis to provide a probe wobble signal on the other axis and summing means for receiving the probe wobble signal at said frequency present on the other axis and the output coefficients of one of the other frequencies and subtract said probe wobble signals therefrom to provide wobble free flaw data which has not been substantially altered by flaw signals at frequency $f_3$.

24. An apparatus as in claim 6 including three phase rotators, one of said rotators being connected to receive the output coefficients $A_1B_1$ corresponding to the frequency $f_1$ and generate an $X_1$ component, a second rotator connected to receive said signal and generate a $Y_1$ component, and a third phase rotator connected to receive the X and Y components and the output coefficients $A_2B_2$ at frequency $f_2$ and generate $X_2$ and $Y_2$ components of the frequency $f_2$, X-Y oscilloscope means for displaying $X_1$ vs $X_2$ and $Y_1$ vs $Y_2$, and means for adjusting said first and second rotators to generate straight line display indications on the oscilloscope display for supports before combining the outputs, whereby to eliminate support indications, especially in the case where support indications from different frequencies do not have the same shape due to skin effect modulation.

25. An eddy current test apparatus including at least one coil adapted to be coupled to an object to be tested to induce eddy currents in said object which in turn induce voltages in said coil or in a sensing coil comprising means for applying excitation signals at frequencies $f_1$, $f_2$ and $f_3$, where $f_3$ is substantially higher than $f_1$ and $f_2$ to said coil to induce eddy currents in said object, means for receiving the voltage induced by the eddy currents in said object in said coil or sensing coil to provide output signals $E_1$ sine $(\omega_1 t + \theta)$, $E_2$ sine $(\omega_2 t + \theta)$ and $E_3$ sine $(\omega_3 + \gamma)$, means connected to receive said output signals and provide Fourier amplitude coefficients $A_1B_1$, $A_2B_2$, $A_3B_3$ representing the coil induced voltages at frequencies $f_1$, $f_2$ and $f_3$ where $A_1 = E_1$ (cosine $\theta$) $B = E_1$, sine $\theta$, $A_2 = E_2$ cosine $\phi$, $B_2 = E_2$ sine $\phi$, $A_3 = E_3$ cosine $\gamma$ and $B_3 = E_3$ sine $\gamma$, rotating means for receiving the Fourier amplitude coefficients $A_3B_3$ to rotate them through an angle in an X-Y coordinate system in which they are coordinates so as to align the indications from near surface flaws as closely as possible with one axis of the coordinate system and summing means for receiving the probe wobble signal on the other axis at said frequency and the output coefficients from one of the other frequencies to subtract the probe wobble signal therefrom to provide a wobble free flaw detection signal which has been substantially unaltered by any flaw data at the frequency $f_3$.

26. An apparatus as in claim 25 including three phase rotators, one of said rotators being connected to receive the output coefficients $A_1B_1$ corresponding to the frequency $f_1$ and generate an $X_1$ component, a second rotator connected to receive said signal and generate a $Y_1$ component, and a third phase rotator connected to receive the X and Y components and the output coefficients $A_2B_2$ at frequency $f_2$ and generate $X_2$ and $Y_2$ components of the frequency $f_2$, X-Y oscilloscope means for displaying $X_1$ vs $X_2$ and $Y_1$ vs $Y_2$, and means for adjusting said first and second rotators to generate straight line display indications on the oscilloscope display for supports before combining the outputs, whereby to eliminate support indications, especially in the case where support indications from different frequencies do not have the same shape due to skin effect modulation.

* * * * *